(12) United States Patent
Geuder et al.

(10) Patent No.: US 8,556,485 B2
(45) Date of Patent: Oct. 15, 2013

(54) LIGHT SOURCE FOR COUPLING LIGHT INTO A MEDICAL HAND-HELD DEVICE

(75) Inventors: Volker Geuder, Heidelberg (DE); René Draheim, Sandhausen (DE)

(73) Assignee: Geuder AG, Heidelberg (DE)

( * ) Notice: Subject to any disclaimer, the term of this patent is extended or adjusted under 35 U.S.C. 154(b) by 377 days.

(21) Appl. No.: 12/937,864

(22) PCT Filed: Mar. 31, 2009

(86) PCT No.: PCT/DE2009/000405
§ 371 (c)(1),
(2), (4) Date: Dec. 14, 2010

(87) PCT Pub. No.: WO2009/127184
PCT Pub. Date: Oct. 22, 2009

(65) Prior Publication Data
US 2011/0090679 A1    Apr. 21, 2011

(30) Foreign Application Priority Data
Apr. 16, 2008    (DE) .......................... 10 2008 019 313

(51) Int. Cl.
*A61B 1/00* (2006.01)
*A61B 3/12* (2006.01)
(52) U.S. Cl.
USPC .......................................... 362/572; 362/577
(58) Field of Classification Search
USPC .................. 362/552, 555, 572, 573, 574, 577
See application file for complete search history.

(56) References Cited

U.S. PATENT DOCUMENTS

| 3,582,638 | A | * | 6/1971 | Peters | ............................ | 362/577 |
| 4,222,375 | A | * | 9/1980 | Martinez | ........................ | 600/249 |
| 5,086,378 | A | * | 2/1992 | Prince | ............................ | 362/103 |
| 5,580,147 | A | | 12/1996 | Salerno | | |
| 6,432,049 | B1 | | 8/2002 | Banta et al. | | |
| 6,786,628 | B2 | * | 9/2004 | Steen et al. | ................... | 362/572 |
| 2004/0027822 | A1 | | 2/2004 | Biro | | |
| 2004/0170014 | A1 | | 9/2004 | Pritchard et al. | | |
| 2006/0256553 | A1 | | 11/2006 | Lin | | |

FOREIGN PATENT DOCUMENTS

| DE | 32 33 410 | 4/1984 |
| DE | 89 00 774 | 5/1989 |
| DE | 299 13 240 | 3/2000 |
| DE | 10 228317 A1 | 1/2004 |
| DE | 20 2007 012 975 | 1/2008 |
| WO | WO 2006/080738 | 8/2006 |

OTHER PUBLICATIONS

English translation of the Written Opinion of the International Searching Authority for International Application No. PCT/DE2009/000405.

(Continued)

*Primary Examiner* — David V Bruce
(74) *Attorney, Agent, or Firm* — Alston & Bird LLP

(57) ABSTRACT

The invention relates to a light source for coupling light into a hand-held medical device, especially a hand-held surgical device, preferably for using in ophthalmology. The light source is characterized by a hand lamp/flashlight provided with a lamp head comprising at least one lamp, and a fiber-optic light guide leading towards the hand-held device. The fiber-optic light guide can be connected to an adapter associated with the lamp head.

18 Claims, 1 Drawing Sheet

(56) References Cited

OTHER PUBLICATIONS

International Prelimary Report on Patentability for Application No. PCT/DE2009/000405 dated Nov. 18, 2010.
International Search Report for International Application No. PCT/DE2009/000405.
Written Opinion (Schriftlicher Bescheid der Internationalen Recherchenbehörde) for International Application No. PCT/DE2009/000405.
European Search Report for Application No. EP2262409, dated Aug. 8, 2013.

* cited by examiner

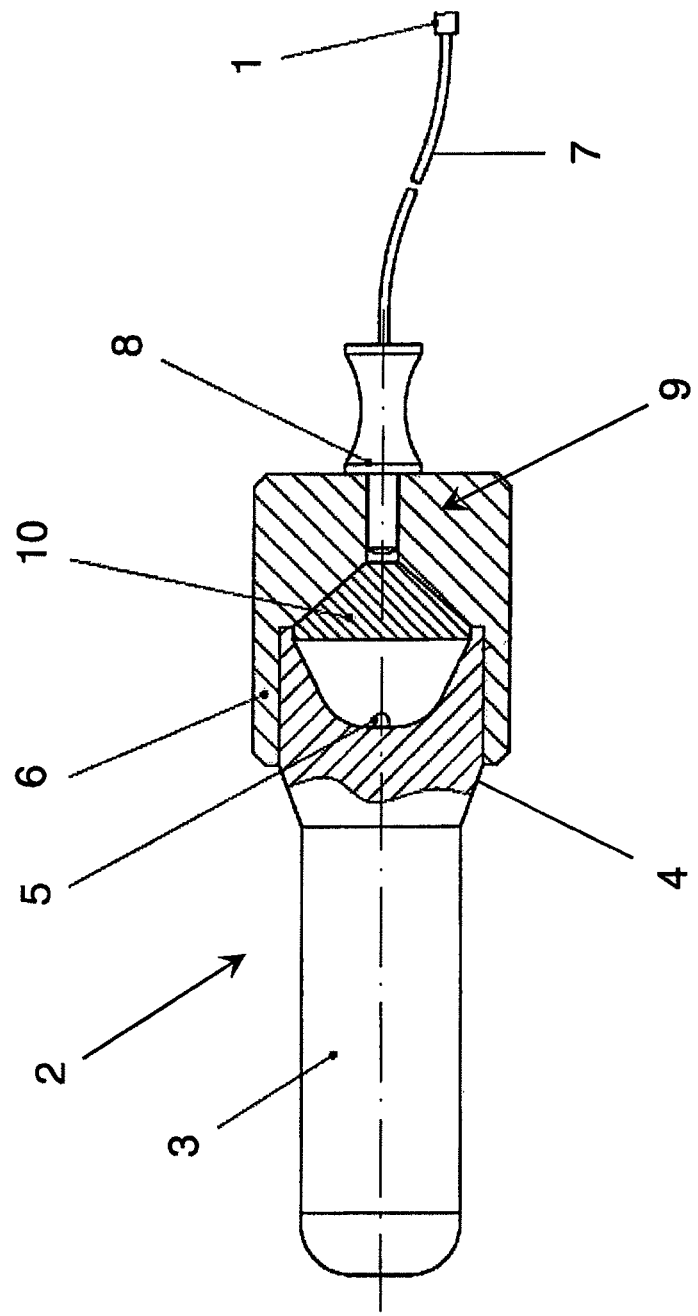

LIGHT SOURCE FOR COUPLING LIGHT INTO A MEDICAL HAND-HELD DEVICE

BACKGROUND OF THE INVENTION

1. Field of the Invention

The invention relates to a light source for coupling light into a medical hand-held device, more particularly, a surgical hand-held device, preferably for use in ophthalmology.

2. Description of Related Art

Light sources for coupling light into medical hand-held devices are well-known in actual practice. The light is generally coupled into the hand-held device by means of an optical fiber, the light being provided by means of a stationary light source. Accordingly, in these cases, an optical fiber extending between the stationary light source and the medical hand-held device is used so that the movability and flexibility of the optical fiber can be utilized to obtain a certain freedom of movement when handling the hand-held device. But the disadvantage here is the mostly stationary arrangement of the light source that necessitates considerable amount of equipment.

It is an object of the present invention to design and develop a light source for coupling light into a medical hand-held device, more particularly, a surgical hand-held device, preferably for use in ophthalmology, such that the light source is more or less mobile so that it can follow the hand-held device or can be moved together with the hand-held device, particularly, when provided with the smallest possible design. Furthermore, the light source is intended to have a simple construction and be reasonably priced, as far as possible.

SUMMARY OF VARIOUS EMBODIMENTS

The above object is achieved according to the invention by a light source as described herein. Accordingly, the category-defining light source is characterized by a hand lamp/flashlight comprising a lamp head having at least one lamp, and a fiber-optic light guide leading to the hand-held device, the fiber-optic light guide being connectable to an adapter assigned to the lamp head.

One finding according to the invention is that a conventional hand lamp/flashlight, namely a flashlight comprising at least one lamp, is suitable for use as a light source for a medical hand-held device. Such a hand lamp/flashlight can be adapted accordingly; namely, it must have a special adapter that is assigned to the lamp head of the hand lamp/flashlight. The optical fiber is connected to the adapter and it extends between the adapter and the hand-held device. It is thus possible, for example, to hold the hand lamp/flashlight in one hand and the hand-held device in the other. It is also feasible for the hand lamp/flashlight to be held by the assistant of a surgeon while the surgeon handles the hand-held device. Apart from the simple construction of a hand lamp/flashlight, the advantages in terms of handling the same are obvious.

In a particularly advantage manner, the hand lamp/flashlight is in the form of a penlight. The hand lamp/flashlight can comprise at least one battery or at least one rechargeable battery. The rechargeable battery could be recharged externally or from the outside when used in the hand-held lamp/flashlight.

In a very advantageous manner, the hand lamp/flashlight is dimmable so that the intensity of the light to be coupled can be adjusted.

The adapter represents the link between the hand lamp/flashlight and the optical fiber. It is therefore of particular advantage when the adapter is plugged, pressed, screwed or glued onto the lamp head. The ability of the adapter to be replaced is an essential advantage. This will be described in detail further below.

The adapter could comprise a special optical system that directly or indirectly adjoins the lamp head. The optical system can be an integral component of the adapter.

Advantageously, the optical system comprises a lens or a lens array. The optical system can act within the meaning of a converging lens in order to focus the light emitted by the lamp head of the hand lamp/flashlight. It is also feasible for the optical system to be configured in the form of a varifocal optical system that can be adjusted from the outside, for example, by means of a knurled wheel provided on the lamp head or on the adapter. In this case, the focal position of the light focused could be altered.

In a further advantageous manner, the adapter comprises a terminal area on that side of the adapter that is oriented away from the lamp head, which terminal area is intended for inserting or plugging on a connector of the fiber-optic light guide or the optical fiber. The connector of the fiber-optic light guide can be inserted into or onto a light channel extending from the optical system up to the free end of the adapter. It is also possible here that a color filter is or can be disposed in the lamp head or in the adapter.

In light of the above remarks, it is very advantageous if adapters comprising various optical systems and/or various filters and/or variable connectivity for connecting different fiber-optic light guides can be replaced. This enables the light source of the invention to be adapted optimally to suit the respective conditions.

It is also feasible for a probe or a lance to be connectable to the adapter for point illumination. Lastly, the adapter can serve for the adaptation of arbitrary fiber-optic light guides, for which purpose it may be necessary to provide very specific connectors for the respective light guide.

As for the lamp head, it is advantageous if lamps of various types are provided in the lamp head. For example, it is possible for the lamps to comprise a plurality of LEDs. The LEDs can, in turn, emit light of various wavelengths so that one or more LEDs can be activated to enable a definition of the resulting spectrum emitted by the LEDs.

It is also feasible for the lamp head to comprise a centrally disposed light bulb and LEDs disposed around the same. The light bulb can be a krypton light bulb by way of example. Any other lamps can also be used.

As for switching the respective lamps on and off or activating the same, it is advantageous if the lamps can be switched on individually or in groups. This again results in a special option of controlling the light intensity on the one hand and the wavelength emitted on the other. The light source of the invention can thus be adapted optimally to suit the respective application.

BRIEF DESCRIPTION OF THE SEVERAL VIEWS OF THE DRAWINGS

There are various possibilities of advantageously carrying out and developing the teaching of the present invention. For this purpose, reference is to be made, on the basis of the drawing, firstly to the various embodiments described herein and secondly to the following explanation of an exemplary embodiment of the light source of the invention for coupling light into a medical hand-held device. Generally preferred embodiments and developments of the teaching are also explained in conjunction with the explanation of the preferred exemplary embodiment of the light source for coupling light into a medical hand-held device. In the drawing, FIG. 1 shows, in a diagrammatic view, an exemplary embodiment of a light source of the invention comprising a fiber-optic light guide connected thereto and a hand-held device, merely suggested in the drawing.

DETAILED DESCRIPTION

As shown in the representation of FIG. 1, the light source serves for coupling light into a medical hand-held device 1 that can be an ophthalmological hand-held device, for example, for point illumination.

According to the invention, the light source comprises a conventional hand lamp 2 that is in the form of a penlight comprising a handle 3 and a lamp head 4 in the exemplary embodiment shown here. At least one lamp 5 is disposed in the lamp head 4.

An adapter 6 is fitted on the lamp head 4, and a fiber-optic light guide 7 can, in turn, be connected by means of a connector 8 to the adapter 6 or inserted into a terminal area 9 of the adapter 6. The fiber-optic light guide 7 extends from the adapter 6 to the hand-held device 1 that is merely suggested in the drawing.

FIG. 1 further clearly shows that the adapter 6 comprises an optical system 10 that is specifically a converging lens in this case. The light, thus focused, travels through the terminal area or a light channel defining the terminal area 9 via the connector 8 into the fiber-optic light guide 7 and from here to the hand-held device 1.

As for the lamps 5, it should be noted that the lamp head 4 can comprise any lamps 5 that can be activated individually or in groups. A filter can also be provided for controlling the wavelength of the light coupled into the fiber-optic light guide 7.

It should be noted once again at this point that the hand lamp 2 can be any commercially available hand lamp. The adapter 6 is configured such that it is adapted to suit the shape and size of the lamp head 4. The terminal area 9 of the adapter 6 is adapted to suit the fiber-optic light guide 7 to be used, and it is possible to provide a variety of adapters 6 for connecting various fiber-optic light guides 7.

It should be further noted that the hand lamp 2 can also be coupled easily to stationary systems, if the latter are equipped with a corresponding adapter for connecting the hand lamp 2. Thus, for example, the hand lamp can also be inserted into a stationary device, from which a fiber-optic light guide can be led to a hand-held device or to an arbitrary location. Of significance, in any case, is the cooperation between the conventional hand lamp 2 and the adapter 6 that basically enables the use of a conventional hand lamp in the form of a light source in the medical field.

As for additional features that are not evident from the FIGURE, reference is made to the general part of the description in order to avoid repetition.

Lastly, it should be noted that the exemplary embodiment described above merely serves to explain the hand-held device of the invention by way of example, but does not limit the same to this exemplary embodiment.

The invention claimed is:

1. A light source for coupling light into a medical hand-held device, said light source comprising:
   a hand lamp/flashlight comprising a lamp head having at least one lamp, and a fiber-optic light guide led to the hand-held device, the fiber-optic light guide being connectable to an adapter assigned to the lamp head,
   wherein the adapter is plugged, pressed, screwed, or glued onto the lamp head, and
   wherein the adapter comprises a terminal area on a side of the adapter that is oriented away from the lamp head, which terminal area is intended for inserting or plugging on a connector of the fiber-optic light guide.

2. The light source according to claim 1 wherein the hand lamp/flashlight is in the form of a penlight.

3. The light source according to 1 wherein the hand lamp/flashlight comprises at least one battery or at least one rechargeable battery.

4. The light source according to claim 1 wherein the hand lamp/flashlight is dimmable.

5. The light source according to claim 1 wherein the adapter comprises an optical system that directly or indirectly adjoins the lamp head.

6. The light source according to claim 5 wherein the optical system comprises a lens or a lens array.

7. The light source according to claim 5 wherein the optical system acts within the meaning of a converging lens.

8. The light source according to claim 5 wherein the optical system is in the form of a varifocal optical system.

9. The light source according to claim 1 wherein the connector of the fiber-optic light guide can be inserted into or onto a light channel extending from the optical system up to the free end of the adapter.

10. The light source according to claim 1 wherein a color filter is disposed or can be disposed in the lamp head or in the adapter.

11. The light source according to claim 1 wherein the adapter comprising various optical systems and/or various filters and/or variable connectivity can be replaced.

12. The light source according to claim 1 wherein a probe or a lance is connectable to the adapter for point illumination.

13. The light source according to claim 1 wherein lamps of various types are provided in the lamp head.

14. The light source according to claim 13 wherein the lamps comprise a plurality of LEDs.

15. The light source according to claim 14 wherein the LEDs emit light of various wavelengths.

16. The light source according to claim 14 wherein the lamp head comprises a centrally disposed light bulb and LEDs disposed around the same.

17. The light source according to claim 16 wherein the light bulb is in the form of a krypton light bulb.

18. The light source according to claim 13 wherein the lamps can be switched on individually or in groups.

* * * * *

UNITED STATES PATENT AND TRADEMARK OFFICE
CERTIFICATE OF CORRECTION

PATENT NO. : 8,556,485 B2  
APPLICATION NO. : 12/937864  
DATED : October 15, 2013  
INVENTOR(S) : Geuder et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 435 days.

Signed and Sealed this

Fifteenth Day of September, 2015

Michelle K. Lee
*Director of the United States Patent and Trademark Office*